United States Patent
Veis et al.

(10) Patent No.: US 12,076,268 B2
(45) Date of Patent: *Sep. 3, 2024

(54) SLEEP APNEA ORAL APPLIANCE WITH CONNECTORS

(71) Applicant: ODIN SLEEP, LLC

(72) Inventors: Robin Veis, Pacific Palisades, CA (US); John Christian, Northridge, CA (US)

(73) Assignee: Odin Sleep, LLC, Chatsworth, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/208,445

(22) Filed: Jun. 12, 2023

(65) Prior Publication Data

US 2024/0115413 A1 Apr. 11, 2024

Related U.S. Application Data

(63) Continuation of application No. 16/966,872, filed on Jul. 31, 2020, now Pat. No. 11,672,690.

(51) Int. Cl.
*A61F 5/00* (2006.01)
*A61C 7/08* (2006.01)
*A61C 7/36* (2006.01)
*A61F 5/56* (2006.01)

(52) U.S. Cl.
CPC ............... *A61F 5/566* (2013.01); *A61C 7/08* (2013.01); *A61C 7/36* (2013.01)

(58) Field of Classification Search
CPC .... A61C 7/08; A61C 7/36; A61C 5/14; A61F 5/37; A61F 5/56; A61F 5/566; A63B 71/085

USPC .... 433/5–8, 19, 24, 140; 128/848, 859, 861, 128/862
See application file for complete search history.

(56) References Cited

U.S. PATENT DOCUMENTS

| 5,980,247 | A | 11/1999 | Cleary |
| 6,109,265 | A | 8/2000 | Frantz et al. |
| 6,526,982 | B1* | 3/2003 | Strong ............ A61F 5/566 128/848 |
| 11,672,690 | B2* | 6/2023 | Veis ............ A61C 7/36 128/848 |
| 2010/0129763 | A1 | 5/2010 | Kuo |
| 2012/0073582 | A1 | 3/2012 | Kopp |
| 2014/0020691 | A1 | 1/2014 | Sweeney et al. |
| 2014/0230829 | A1 | 8/2014 | Rogers |
| 2014/0326253 | A1 | 11/2014 | Baratier |

(Continued)

OTHER PUBLICATIONS

PCT/US2019/016198. International Preliminary Report on Patentability issued Aug. 4, 2020. (6 pages).

(Continued)

*Primary Examiner* — Adam Baker
(74) *Attorney, Agent, or Firm* — LOZA & LOZA, LLP; Michael F. Fedrick

(57) ABSTRACT

An oral appliance having an upper dental tray and lower dental tray. The upper dental tray and lower dental tray are connected by an elongated connector having receptacles at its proximal and distal ends for engaging laterally extending supports on the upper dental tray and lower dental tray, respectively. A backstop is positioned adjacent to each of the laterally extending supports to prevent movement of the connector in a predetermined direction.

24 Claims, 13 Drawing Sheets

(56) References Cited

U.S. PATENT DOCUMENTS

2017/0367793 A1 12/2017 Veis
2018/0153643 A1 6/2018 Lambert

OTHER PUBLICATIONS

PCT/US 2019/016198. International Search Report mailed May 23, 2019. (7 pages).

Ken Berley, et al., "A New Lease on Life with the Silent Nite® Sleep Appliance: How Dentists are Helping Patients Overcome Sleep-Disordered Breathing," Chairside Magazine, vol. 14, Issue 3, Sep. 25, 2019.

"Silent Nite® Slide-Link," https://web.archive.org/web/20171211174445if_/http://www.endsnore.com/silent-nite-snoring-prevention-device.aspx, downloaded to the Internet Archive on Dec. 11, 2017.

"EMA First Step," https://web.archive.org/web/20170610224736/http://www.myersontooth.com/products/ema-first-step.php, downloaded to the Internet Archive on Jun. 10, 2017.

"OPTISLEEP," downloaded from https://www.sicat.com/products/sleep-medicine/optisleep/ on May 27, 2021.

\* cited by examiner

SLEEP APNEA ORAL APPLIANCE WITH CONNECTORS

CROSS-REFERENCE TO RELATED APPLICATIONS

This application claims the benefit of priority under 35 U.S.C. § 119(e) from U.S. Patent Application No. 62/624,730, filed on Jan. 31, 2018 and entitled SLEEP APNEA ORAL APPLIANCE WITH CONNECTORS, and under 35 U.S.C. § 120 from U.S. patent application Ser. No. 16/966,872 filed on Jul. 31, 2020, which is the US national stage of PCT/US2019/016198 filed on Jan. 31, 2019. The disclosures of the foregoing applications are incorporated herein by reference in their entireties.

BACKGROUND

Sleep apnea is a disorder characterized by abnormal pauses in breathing or instances of abnormally low breathing during sleep. Each pause in breathing, called an apnea, can last from a few seconds to minutes (typically lasting 20 to 40 seconds) and may occur 5 to 30 times or more an hour. Sleep apnea results from a partial-to-complete blockage of a subject's airway. Increased air speed through the airway causes an increase in dynamic pressure and a corresponding drop in static pressure. The decreased static pressure can in some instances draw back the lower jaw and tongue and thereby block the airway. This blockage can increase to the point of becoming complete, which at least temporarily interrupts breathing.

Subjects are generally at greater risk for sleep apnea if they are overweight or have conditions such as diabetes, hypertension, or chronic nasal congestion. There are a variety of factors, however, which can lead to sleep apnea. One factor is the presence of a narrow maxilla and/or mandible in a subject. Maxillary constriction may increase nasal resistance and alter the tongue posture, leading to narrowing of the retroglossal airway. Constriction of the maxilla and/or the mandible generally reduces intraoral air volume and tends to force the tongue back into the posterior airway space, leading to obstructive sleep apnea during sleep.

Orthodontics is a field of dentistry which focuses on the repositioning of a subject's teeth and jaws for aesthetic or other reasons, for example due to the "overcrowding" of a subject's teeth. Orthodontic methods typically require a subject to make continuous use of a dental appliance for a period of time in order to achieve results. The use of such appliances precludes the concurrent use of currently available oral appliances for treating sleep apnea. There remains a need therefore for improved devices and methods for treating sleep apnea, including in users of orthodontic appliances who experience sleep apnea.

SUMMARY

An oral appliance for treating snoring and/or sleep apnea in a subject is disclosed which generally comprises an upper dental tray, a lower dental tray, and a pair of connectors which mechanically join the upper and lower dental trays. The upper dental tray and lower dental tray each have an anterior portion, a posterior portion, a right side, a left side, a buccal side, a lingual side, and an exterior surface, as well as generally comprising a receptacle portion, a right side connector mount, and a left side connector mount. The receptacle is bounded by the inner surface of the upper dental tray and receives the subject's maxillary or mandibular dentition, as the case may be, or corresponding orthodontic trays.

The connector mounts each include a laterally extending support having a proximal end secured to a dental tray and a distal end that includes a flange. The flange can have a circular outer rim and preferably extends circumferentially around the distal end of the laterally extending support. The backstop of the connector mounts is likewise secured to the dental tray, and includes an engagement surface facing but spaced apart from the laterally extending support. The engagement surface is preferably planar or substantially planar, but can also be radiused. The right side connector of the upper dental tray is mount is connected to the right side exterior surface of the upper dental tray on the buccal side of the upper dental tray, while the left side connector mount is attached to the left side exterior surface of the upper dental tray on the buccal side of the upper dental tray. Likewise, the right side connector mount of the lower dental tray is connected to the right side exterior surface of the lower dental tray on the buccal side of the lower dental tray, while the left side connector mount is attached to the left side exterior surface of the lower dental tray on the buccal side of the lower dental tray.

The appliance further includes right side and left side connectors, each having a proximal end, a distal end, an inner surface, an outer surface, an upper surface, a lower surface, a first lateral side, a second lateral side, an interior channel between the first lateral side and the second lateral side, a first receiving portion at the proximal end having a first opening, and a second receiving portion at the distal end having a second opening, with the receiving portions preferably comprising at least one projection which extends inwardly from the interior surface of the connector. The laterally extending supports of the connector mounts fit within the openings of the receiving portions so that the exterior surface of a laterally extending support faces the interior surface of a respective end of the connector and the exterior surface of the respective end of the connector faces the engagement surface of the backstop. The flange of the laterally extending support preferably has a lower surface facing the upper surface of a connector when the connector is attached to the connector mount. The lateral sides of the connectors can also comprise first and second lateral members which are curved.

The connector mounts of the upper dental tray and/or the lower dental tray can be integrally formed with the upper dental tray. Alternatively, the laterally extending support and the backstop of one or more of the connector mounts can be attached to and/or integrally formed with a base which is secured to the upper dental tray or the lower dental tray.

FIGURES

Figure 1:
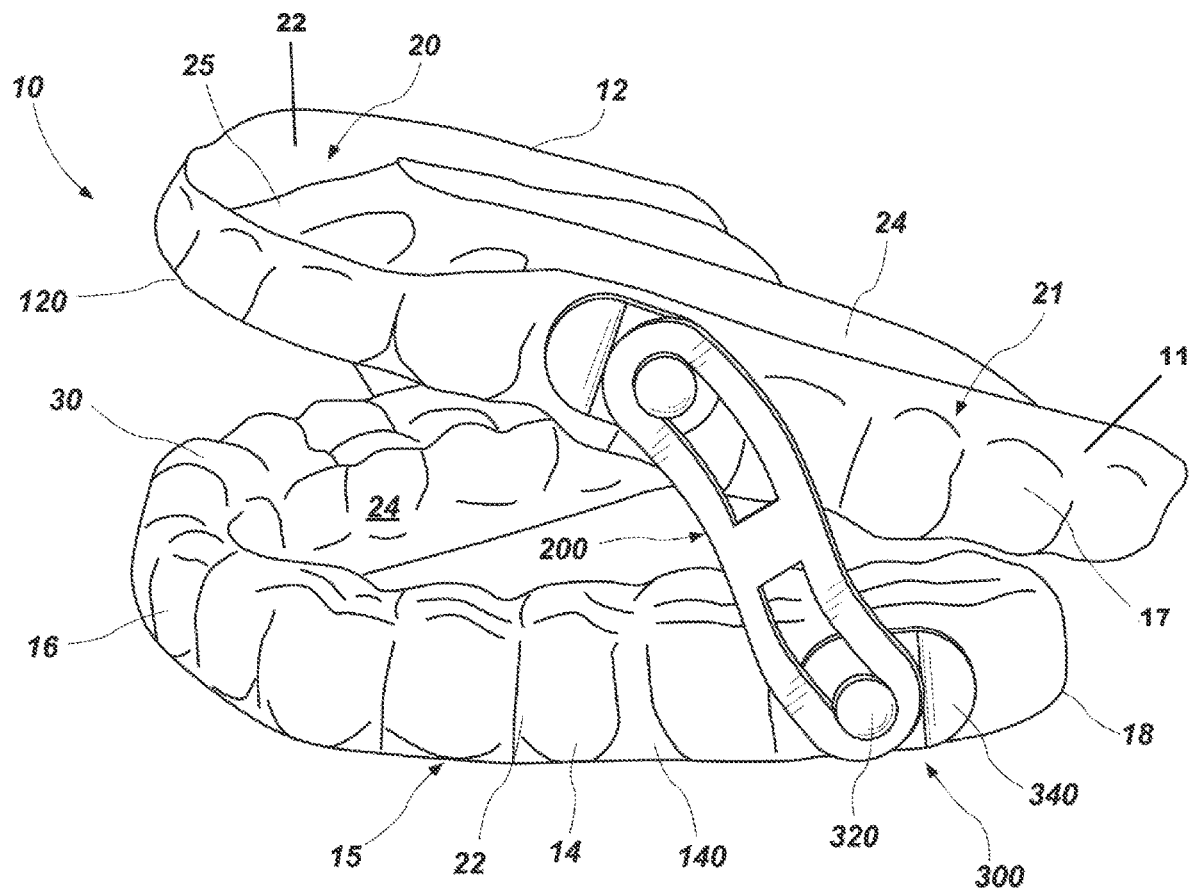
FIG. 1 is a left side perspective view of an embodiment of the present appliance with connectors.

| Component | Subcomponent | Reference Number |
|---|---|---|
| appliance | | 10 |
| dental trays | | 15 |
| | dental tray buccal side | 11 |
| | dental tray lingual side | 13 |
| | dental tray right side | 12 |
| | dental tray left side | 14 |
| | dental tray anterior portion | 16 |
| | dental tray posterior portion | 18 |
| | dental tray exterior surface | 17 |
| dental tray receptacle | | 20 |
| | receptacle lateral walls | 21 |
| | receptacle buccal wall | 22 |
| | receptacle labial wall | 24 |
| | receptacle interior surface | 25 |
| | upper dental tray | 120 |
| | lower dental tray | 140 |
| connector | | 200 |
| | connector opening | 201 |
| | connector proximal end | 202 |
| | connector distal end | 204 |
| | connector first lateral side | 206 |
| | connector second lateral side | 208 |
| | connector receiving portion | 210 |
| | connector first receiving portion | 211 |
| | connector opening | 212 |
| | connector second receiving portion | 213 |
| | connector inner surface | 214 |
| | connector lateral member | 215 |
| | connector first lateral member | 216 |
| | connector second lateral member | 218 |
| | connector lateral member upper surface | 217 |
| | connector lateral member lower surface | 219 |
| | retaining members | 220 |
| | connector interior channel | 230 |
| | connector first interior channel | 231 |
| | connector second interior channel | 233 |
| | connector brace | 235 |
| connector mount | | 300 |
| | connector mount base | 310 |
| | connector mount upper surface | 312 |
| | connector mount lower surface | 314 |
| | connector mount proximal end | 316 |
| | connector mount distal end | 318 |
| | connector mount laterally extending support | 320 |
| connector mount post | | 322 |
| | connector mount post proximal end | 321 |
| | connector mount post distal end | 323 |
| | connector mount post outer surface | 325 |
| | connector mount post flange | 330 |
| | connector mount post flange lower surface | 331 |
| | connector mount post flange circular outer rim | 332 |
| connector mount backstop | | 340 |
| | connector mount backstop engagement surface | 342 |
| | connector mount backstop exterior surface | 344 |

Definitions

Description

As used herein, the following terms and variations thereof have the meanings given below, unless a different meaning is intended by the context in which such term is used. Terms relating to location and orientation (e.g., "upper," "lower," "right," "left," "exterior," "interior," "anterior," "posterior," etc.) are to be understood as being relative and not absolute terms. For example, "right" and "left" will thus be used to designate opposing lateral sides of components of the present article of manufacture. For convenience, these terms are generally used with reference to the placement or orientation of the appliance or a component thereof when the appliance is worn by a subject.

"About" and "approximately" refer to a quantity or distance within 10% of the referenced quantity or distance, unless the circumstances of such usage would indicate a different meaning.

"Anterior" means in the direction of or toward or adjacent the front portion (opening) of a subject's mouth when the present appliance is worn by a subject.

"Backstop" refers to a component or structure prevents movement or further advancement of another component or structure.

"Buccal" means in the direction of or toward a subject's cheek when the present appliance is worn by a subject. In relation to a subject's teeth, this refers to the side of the teeth facing the cheek.

"Coronal plane" refers to a hypothetical planar surface that extends through the body from the head to the feet, and divides the body into front and rear halves.

"Coronal" refers to a position or direction which is on or toward the distal end of a tooth (i.e., where the biting surface is located). A coronal surface is thus the biting surface of a tooth, which in posterior teeth is generally referred to as an occlusal surface and on anterior teeth is called an incisal surface.

"Dental tray" refers to a structure comprising a receptacle for receiving the teeth of a subject and/or for receiving an orthodontic tray worn on a subject's teeth. The receptacle has an opening for receiving teeth or orthodontic trays worn and an interior surface which contacts the subject's teeth or orthodontic trays worn by the subject.

"Downward" and "downwardly" mean in the direction of or toward a lower portion of a subject's body when the present appliance is worn by a subject. "Upward" and "upwardly" mean in the opposite direction, i.e. in the direction of or toward an upper portion of a subject's body.

"Elongated" refers to a configuration or shape having a length which is longer than its width.

"Flange" refers to a projecting rim, collar, or rib on an object

"Horizontal," with respect to the present appliance, refers to disposition in a plane approximately perpendicular to the sagittal and/or the coronal plane of a subject, i.e. within 15 degrees of such a perpendicular plane, when the present appliance is worn by a subject.

"Labial" means in the direction of, toward, or adjacent to a subject's lips when the present appliance is worn by a subject. In relation to a subject's teeth, this refers to the side of the front teeth facing the lips.

"Lateral" means away from the sagittal plane of a subject when the present appliance is worn by a subject.

"Left" means to the left of the center sagittal plane of a subject, from the perspective of the subject when the present appliance is worn by a subject.

"Lingual" means in the direction of, toward, or adjacent to a subject's tongue when the present appliance is worn by a subject. In relation to a subject's teeth, this refers to the side of the teeth facing the tongue.

"Lower" refers to the relative position of a component in the present appliance which is closer to or toward a lower portion of a subject's body when the present appliance is worn by a subject.

"Mandibular" refers to the lower jaw.

"Mandibular dentition" refers to the teeth of the lower jaw.

"Maxillary" refers to the upper jaw.

"Maxillary dentition" refers to the teeth of the upper jaw.

"Mechanically connected" means physically connected, either through a connection based on direct physical contact or via another structure.

"Medial" means toward the center sagittal plane of a subject when the present appliance is worn by a subject.

"Mount" (as a verb) refers to the placement of a component, in this case a connector, on or around another component, such as a support, such that at least a portion of the mounted component (connector) is thereby located proximally of the most distal portion of the support.

"Orthodontic" refers to a feature or an appliance which repositions the teeth and/or jaw(s) of a subject.

"Post" refers to a component which protrudes from a surface and functions as a point of attachment for another component.

"Posterior" means in the direction of or toward or adjacent the rear portion of a subject's mouth when the present appliance is worn by a subject.

"Receptacle" refers to an object or space used to contain something.

"Right" means to the right of the center sagittal plane of a subject when the present appliance is worn by a subject.

"Sagittal plane" refers to an imaginary plane that travels vertically from the top to the bottom of the body of a subject, dividing it into left and right portions.

"Soft plastic" refers to a polymer material capable of elastic deformation upon the application of a force to the plastic, i.e. a temporary shape change that is self-reversing after the force is removed, so that the object returns to its original shape.

"Subject" refers to a user of the present appliance, usually a human user.

"Support" refers to a component or structure that receives a force from another component of structure and remains fixed under normal or expected operating conditions.

"Thermoplastic" refers to a material, generally a polymer material, which may be softened by heat and hardened by cooling in a reversible physical process. The thermoplastic materials used in some components of the present appliance retain their shape at 100° F. and preferably become soft (deformable) at a temperature of 212° F. or below.

"Tray" and "dental tray," as used herein, refer to a generally U-shaped portion of the present appliance comprising an open area for receiving the maxillary or mandibular teeth of a subject, or for receiving orthodontic trays worn by a subject, as the case may be.

"Upper" refers to the relative position of a component in the present appliance which is closer to or toward an upper portion of a subject's body when the present appliance is worn by a subject.

"Vertical," with respect to the present appliance, refers to disposition in a plane approximately parallel to the sagittal and/or the coronal plane of a subject, i.e. within 15 degrees of such a parallel plane. Preferably, vertical refers to a direction toward or away from a subject's head or feet when the present appliance is worn by a subject.

The term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise.

Oral Appliance

The present appliance 10 addresses a long standing need for an appliance which allows lateral movement of a subject's jaws without the risk of dislodging connectors that attach an upper dental tray to a lower dental tray. The present appliance 10 thereby allows a subject using the appliance to open and close the subject's mouth in comfort without dislodging the appliance. This is important in particular for users who are lateral bruxers (i.e., who grind their teeth during sleep in a side-to-side manner), as it doesn't inhibit the ability to move the jaw laterally, but at the same time prevents or inhibits the mandible from dropping backwards and causing snoring and/or apnea.

The present appliance 10 generally comprises a pair of dental trays 15, an upper tray 120 and a lower tray 140, which cooperate to position a subject's jaws so as to avoid sleep apnea. The upper tray 120 is fitted onto a subject's maxillary dentition, while the lower tray 140 is fitted to the subject's mandibular dentition. The trays 15 of the present device each comprise a right side 12, a left side 14, a buccal side 13, a lingual side 15, an anterior portion 16, a posterior portion 18, an exterior surface 17, and a generally U-shaped tooth-receiving receptacle 20 formed on one horizontal side of the tray 15 to fit over a subject's dentition, in the manner of conventional orthodontic devices, or over orthodontic trays such as those sold under the brand name INVISALIGN and made by Align Technology, Inc. The receptacle 20 is configured to receive the teeth (or an orthodontic tray) of a subject and to contact teeth (or an orthodontic tray) on an interior surface 25. The receptacle 20 comprises lateral walls 21 extending from a bottom surface facing the coronal surfaces of a subject's teeth toward the maxilla or mandible, respectively, i.e. buccal wall 22 and lingual wall 24, so as to cover some or all of the buccal and lingual sides of some or all of a subject's teeth. The exterior portions of the trays 15 further comprise a coronal surface 30 formed on the horizontal side of the tray opposite the receptacle 20, i.e. on the exterior of the tray 15. The trays 15 can preferably be formed to conform to a subject's pre-existing dentition or to an orthodontic tray, or in a preferred embodiment the trays 15 can be formed to accomplish a change in the existing dentition and/or in the shape of a subject's mandible and/or maxilla in the manner of an orthodontic appliance, as described further below.

Figure 2:
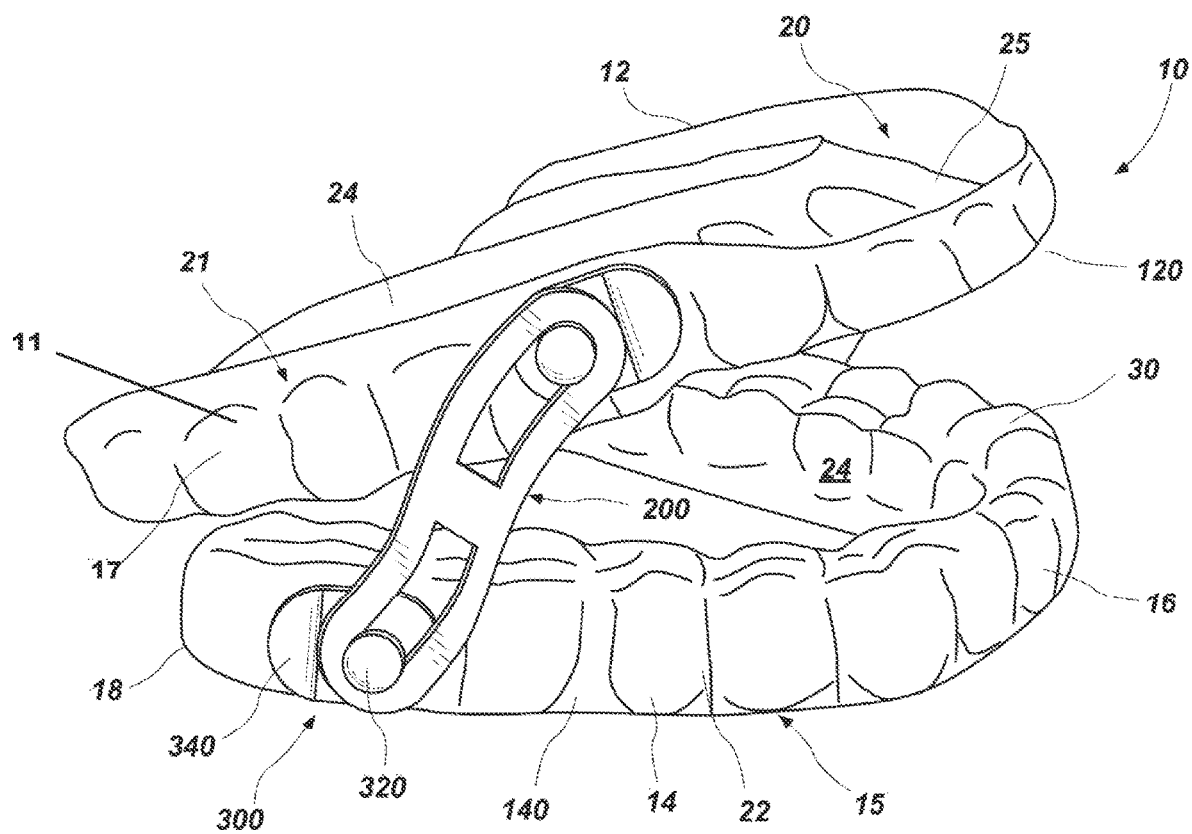
FIG. 2 is a right side perspective view of the appliance of FIG. 1.
Figure 3:
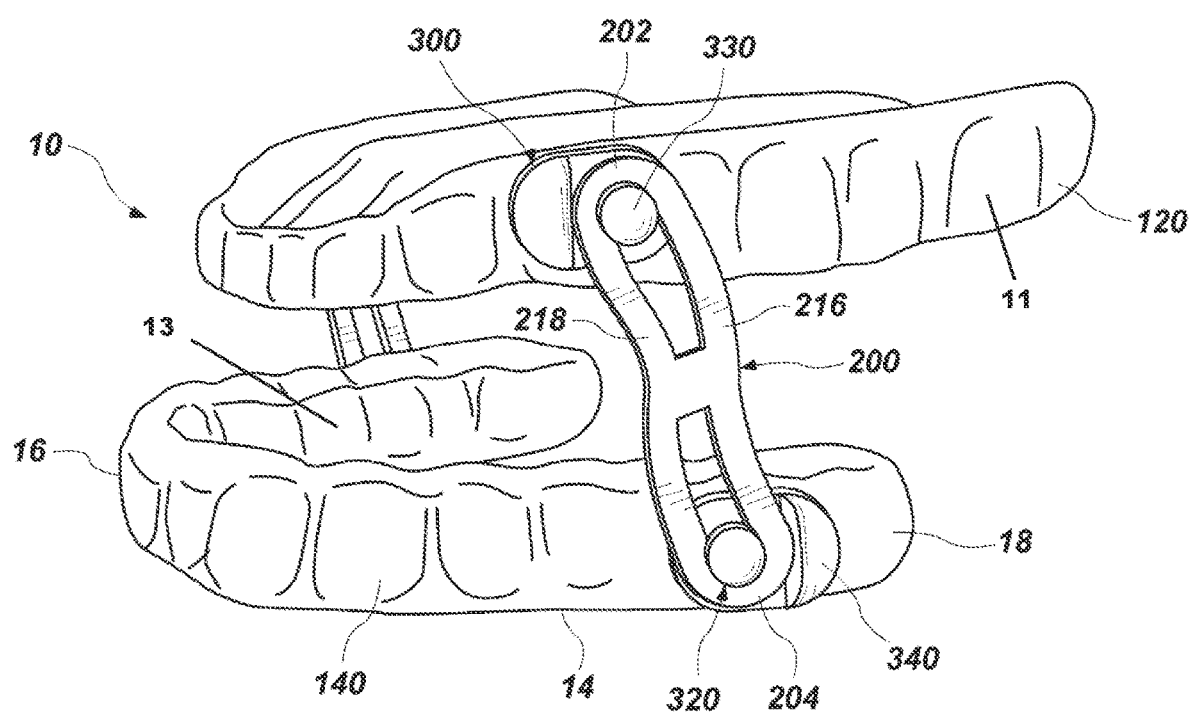
FIG. 3 is a left side elevation view of the appliance of FIG. 1.
Figure 13:
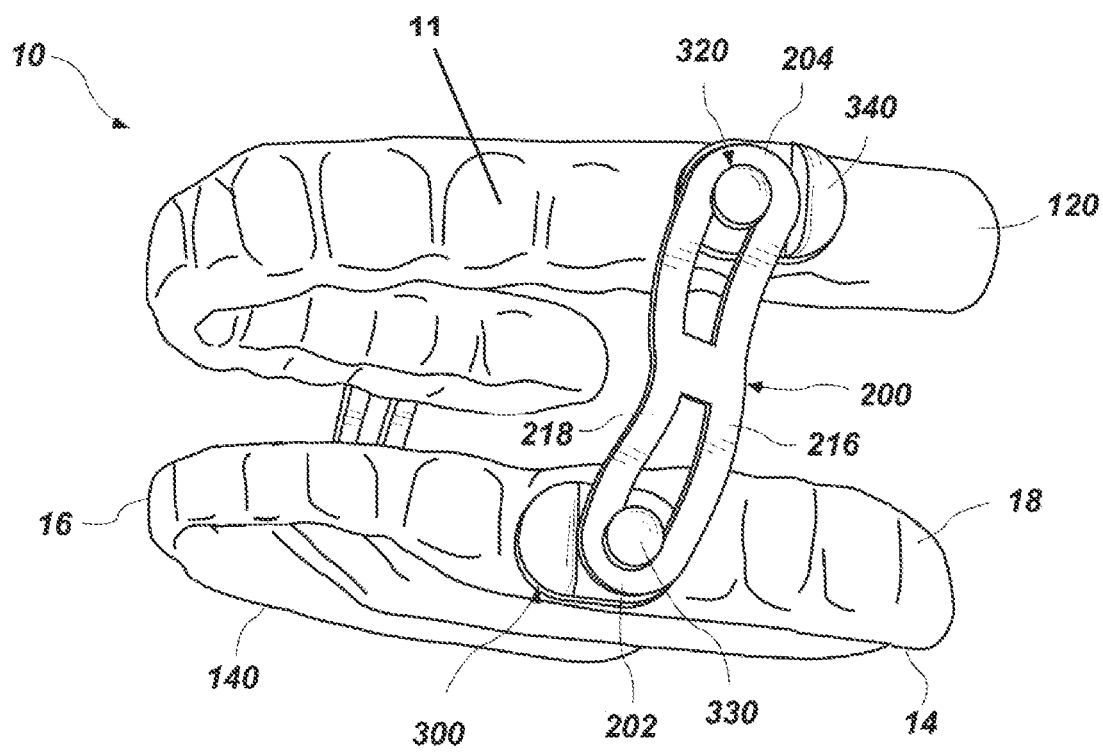
FIG. 13 is a left side perspective view of an alternative embodiment of the present appliance The reference numbers in the drawings designate the following components of the present appliance.

The upper tray 120 and lower tray 140 are mechanically connected to each other through the use of connectors 200 and connector mounts 300. A connector mount 300 is attached to or integrally formed with the upper tray 120 and lower tray 140 on each lateral side of each of these trays, facing buccally outwardly, such that a connector mount 300 is attached on the right side 12 and left side 14 of the upper tray 120 and also on the right side 12 and left side 14 of the lower tray 140. As shown in FIGS. 1-3, in order to maintain a user's mandible in a relatively forward position with respect to the maxilla and thereby treat the user's snoring and/or apnea, the connector mounts 300 are positioned in the upper tray 120 in a relatively anterior position, such as adjacent to a user's cuspid and/or first bicuspid on the right and left side, respectively. The connector mounts 300 are then positioned in the lower tray 140 in a relatively posterior position, such as adjacent to a user's first or second molar. In an alternative embodiment, shown in FIG. 13, the relative position of the connector mounts 300 on the upper dental tray 120 and lower dental tray 140 can be reversed, with the connector mount 300 of the upper tray 120 positioned in a relatively posterior position and the connector mount 300 of the lower tray 120 positioned in a relatively anterior position.

Figure 8:
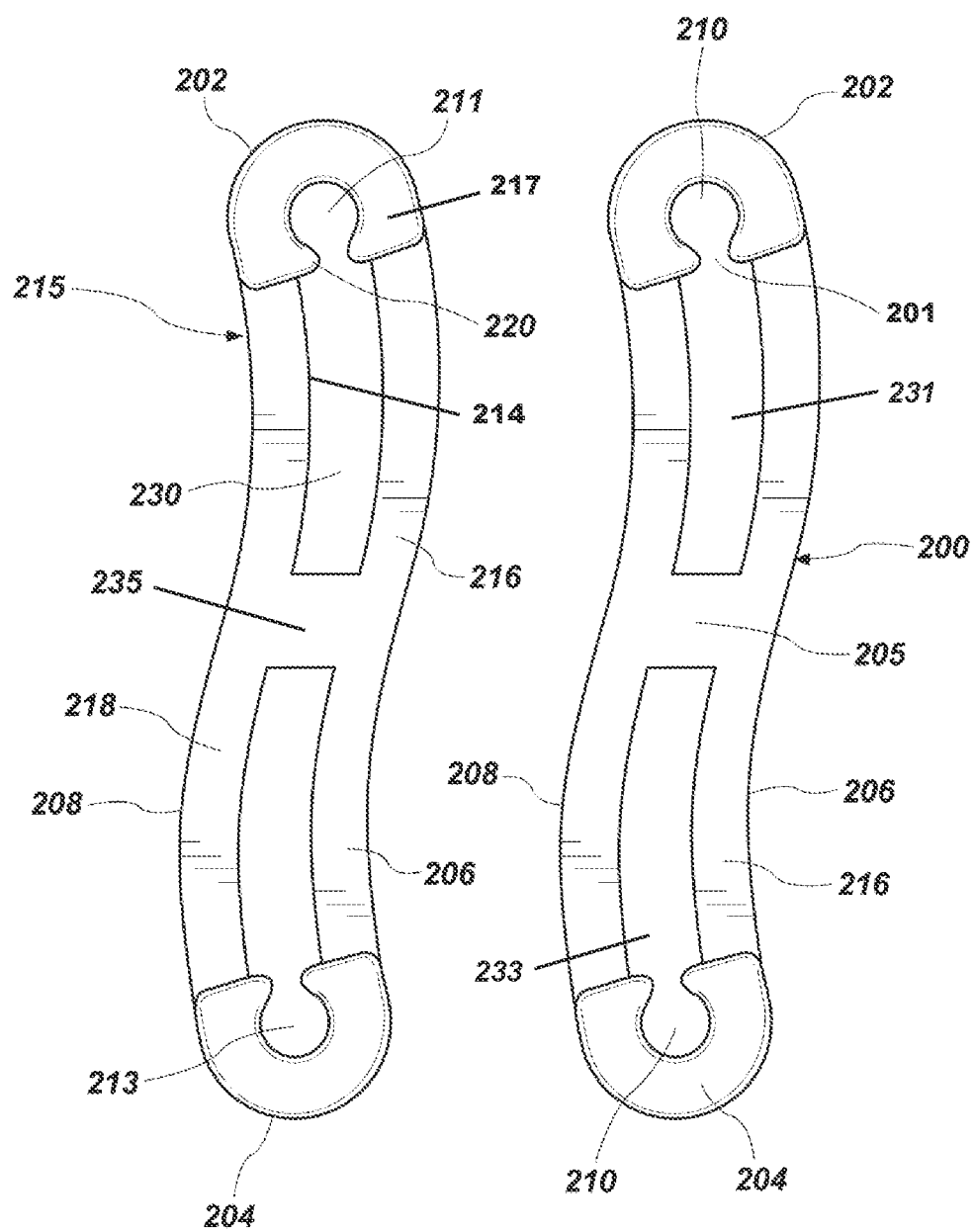
FIG. 8 is a top plan view of a pair of connectors in one embodiment.
Figure 9:
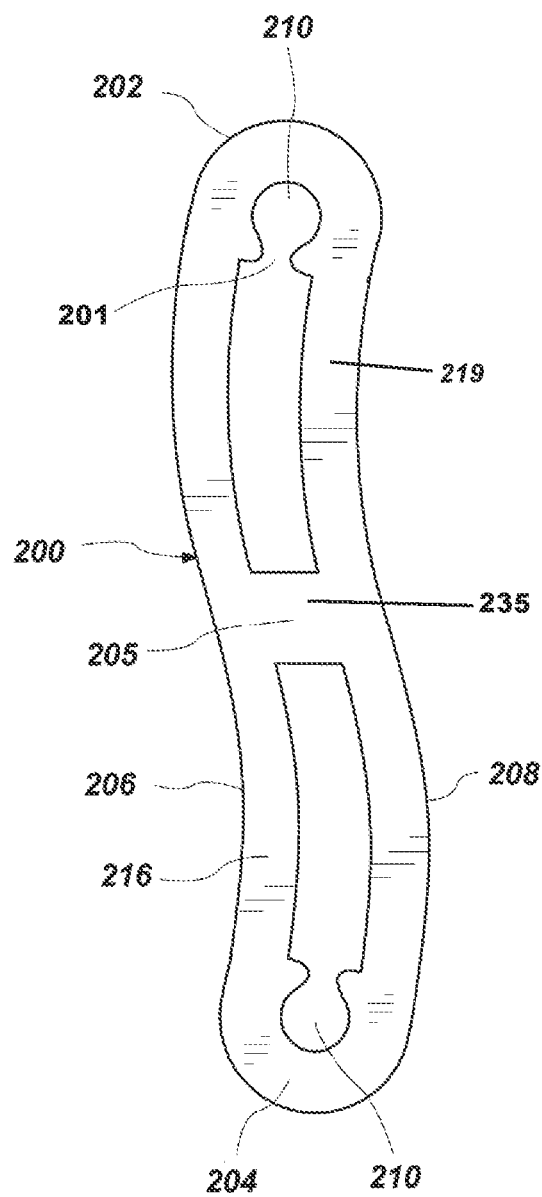
FIG. 9 is a bottom plan view of one of the connectors of FIG. 8.

The connectors 200, best seen in FIGS. 8 and 9, comprise an elongated form having a proximal end 202, a distal end 204, a first lateral side 206, a second lateral side 208, an upper surface 217, a lower surface 219, and two lateral members 215. The connectors can be formed from materials known to the art, such as thermoplastic or other polymer materials. A first lateral member 216 extends from the proximal end 202 to the distal end 204 on one lateral side of the connector 200, while a second lateral member 218 extends from the proximal end 202 to the distal end 204 on the other lateral side of the connector. The first and second lateral members 216, 218 are connected and/or attached to each other at the proximal and distal ends of the connector, respectively, and form the outer boundaries of an interior channel 230. The interior channel 230 receives and retains a post 322 of a laterally extending support 320 attached to a tray 15, as described further below. The first and second lateral members 216, 218 can be straight or curved, but an approximately equal distance is preferably maintained between the inner surfaces 214 of the first and second lateral members 216, 218 along their longitudinal extents.

Some embodiments can include a plurality of interior channels 230. As shown in FIGS. 8, for example, the connector can comprise a first interior channel 231 which is separate from a second interior channel 233. In the embodiment of FIGS. 8 and 9, the first interior channel 231 and second interior channel 233 are separated by a brace 235 which extends between the first lateral member 216 and the second lateral member 218 in a medial portion 205 of the connector 200 between the proximal end 202 and distal end 204. The brace 235 is a support to help maintain a predetermined distance between the inner surface 214 of the first lateral member 216 and the inner surface 214 of the second lateral member 218 in the first and second interior channels 231, 233, in order to allow sufficient room for movement of the post 322 therein.

Figure 4:
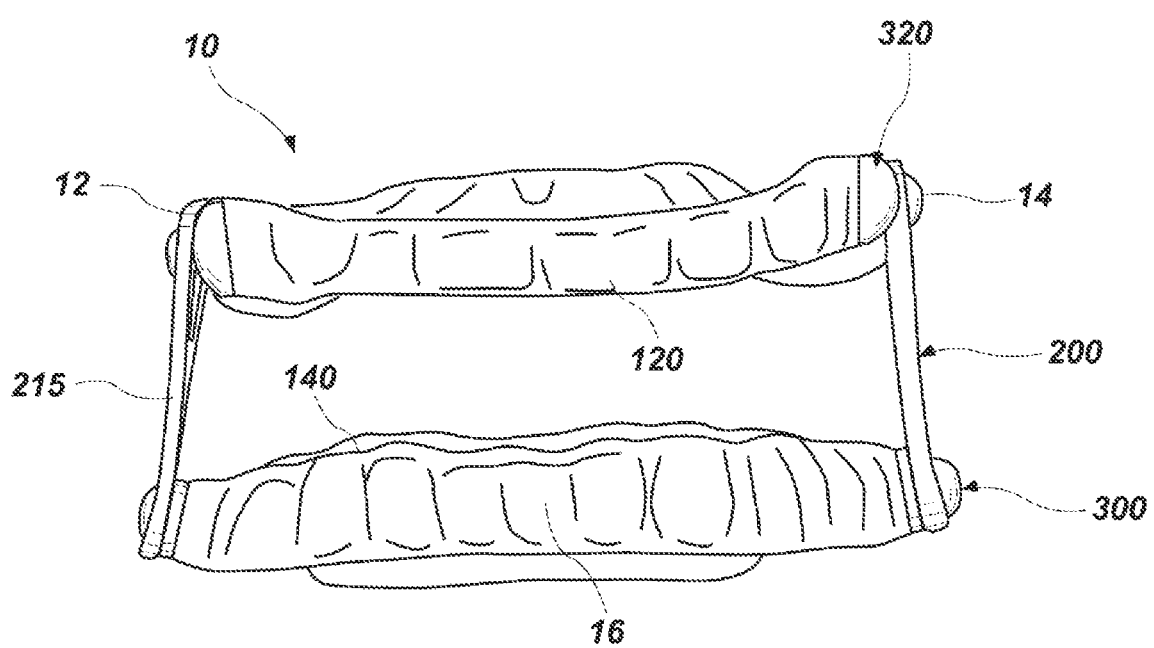
FIG. 4 is a front elevation view of the appliance of FIG. 1.

Each of the proximal end 202 and the distal end 204 of the connector 200 further includes a receiving portion or partial enclosure 210. The receiving portion 210 has an opening 201 to provide communication between the interior of the receiving portion 210 and the interior channel 230. In the embodiment of FIG. 4, the proximal end 202 of the connector 200 comprises a first receiving portion 211 and the distal end 204 comprises a second receiving portion 213. The receiving portions 210 are sized and configured to receive and retain the post 322 of a connector mount 300 in order to mechanically connect and flexibly attach the upper tray 120 and the lower tray 140. The receiving portions 210 preferably include at least one retaining member 220, preferably an inwardly extending projection, in order to better retain the post 322 within the receiving portion 210. In the embodiment of FIGS. 8 and 9, the receiving portions 211, 213 each have a pair of retaining members 220 adjacent the opening 201 between the receiving portion 210 and the interior channel(s) 230. The retaining members 220 in this embodiment comprise projecting structures ("tips") which extend inwardly from each lateral member 216, 218, such as from the inner surface 214 of the respective lateral members 216 and 218. The retaining members 220 have sufficient rigidity to retain a post 322 within the receiving portion 210 until a predetermined amount of force is applied to the connector 200 and/or the post 322 to urge the post 322 into the interior channel 230, but are also preferably sufficiently flexible (i.e., elastically deformable) to be flexed when a sufficient force is applied. The retaining members 220 and/or lateral members 216, 218 together are sufficiently flexible to allow the post 322 to be moved out of the receiving portion 210 into the interior channel 230 without breaking or exceeding the elastic limit of the retaining members 220. In alternative embodiments, a single inwardly extending retaining member 220 can be used, or the retaining members can be left out. A narrowing of the interior channel 230 at the opening 201 of the receiving portion to a distance which is less than the diameter of the post 322 can alternatively be included in the connector 200 in place of the retaining members 220.

Figure 6:
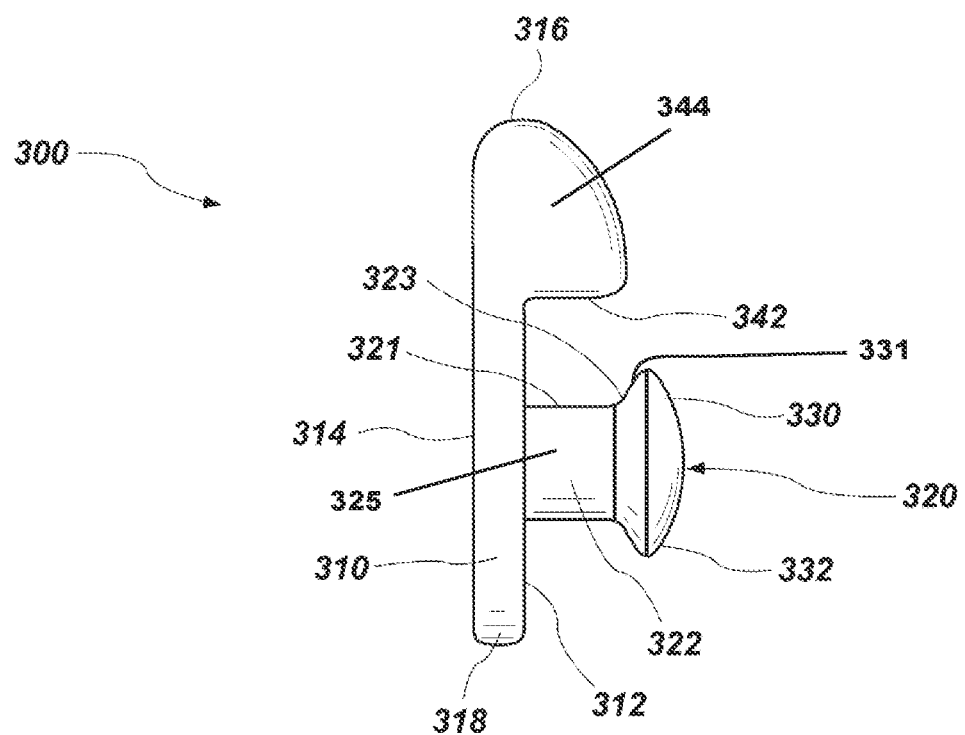
FIG. 6 is a side elevation view of an embodiment of a connector mount having a base.
Figure 7:
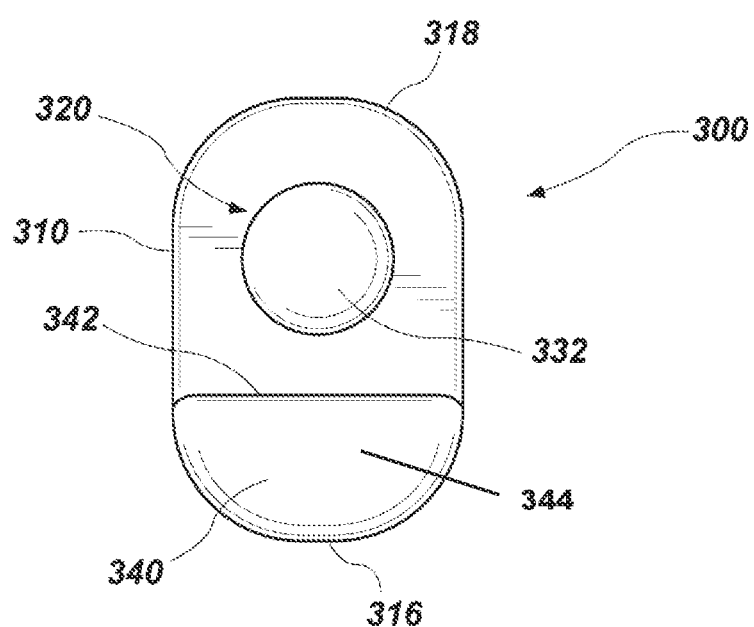
FIG. 7 is a top plan view of the connector mount of FIG. 6.
Figure 12:
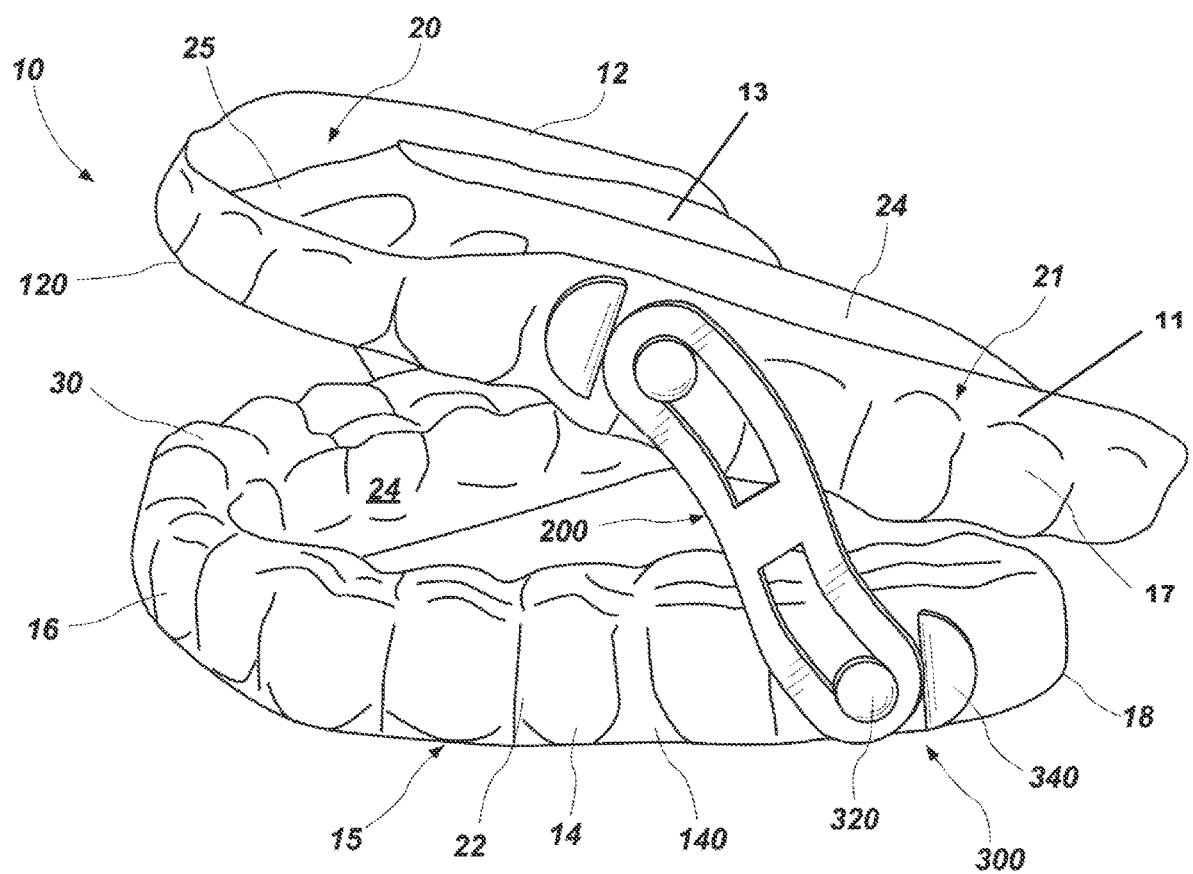
FIG. 12 is a left side perspective view of an embodiment of the present appliance with integrally formed connector mounts.

The connectors 200 mechanically connect the upper tray 120 and the lower tray 140 by means of connector mounts 300 attached on each lateral side of a tray 15. The connector mounts 300 each generally comprise a laterally extending support or post 320 and a backstop 340. In the embodiment shown in FIGS. 1-3, 6 and 7, the illustrated connector mount 300 further comprises a base 310 having an upper surface 312, a lower surface 314, a proximal end 316, and a distal end 318. However, it is to be understood that the laterally extending support 320 and backstop 340 can be directly attached to or integrally formed with the respective lateral surface of a dental tray 15, as long as these structures are sufficiently strong to retain a connector 200 and maintain a connection between the upper tray 120 and the lower tray 140 as described herein. Preferably, the laterally extending support 320 and backstop 340 are integrally formed with each tray 15 when the tray 15 is manufactured, as shown in FIG. 12. In the embodiments of FIGS. 6 and 7, the connector mount 300 is shown as a separate structure that can be manufactured separately from the dental trays 15. In such an embodiment, the base 310 maintains the laterally extending support 320 and backstop 340 in the appropriate respective positions, as well as providing support to these structures.

The laterally extending support 320 of the connector mount 300 generally comprises a post 322 which extends laterally outwardly from each lateral side of a tray 15, i.e. buccally when the present appliance 10 is worn by a subject. The post 322 has a proximal end 321 attached to the base 310 or directly to a tray 15, as the case may be, and a distal end 323 located distally outward from the tray surface along the longitudinal extent of the post 322. Preferably, the distal end 323 of the post 322 comprises a flange 330 which extends laterally (with respect to the longitudinal extent of the post 322) and outwardly in order to better be retained by the receiving portion 210 of a connector 200. In the embodiments illustrated in FIGS. 6, 10, and 11, the flange 330 extends circumferentially around the distal end of the post 322 and has a circular outer rim 332, thereby forming a "button." The post 322 is sized so that its width no more than, and preferably less than, the distance between the lateral members 215, so that the post 322 fits within and can be retained within the interior channel 230 of the connector 200. The distance between the proximal end 321 and distal end 323 of the post 322 is also at least as long as the thickness of the lateral members 215, i.e. the distance between the upper surface 217 and lower surface 219 of a respective lateral member 215. The diameter of the flange 330 is preferably wider than the distance between the inner surface 214 of the first lateral member 216 and the inner surface 214 of the second lateral member 218 when the connector 200 is not under tension (i.e., being elastically deformed), so that when the post 322 is positioned within the interior channel 230 and or within the receiving portion 210, at least a portion of the outer edges of the flange 230 extend beyond the inner surfaces 214 of one or both lateral members 215, i.e. such that the lower surface of the flange 230 is touching or adjacent to the upper surface 217 of one or both lateral members 215. The lateral members 215 and laterally extending support 320 are preferably configured such that the first lateral member 216 and the second lateral member 218 can be flexed, bent or stretched apart from each other sufficiently to be able to fit over the flange 330, in order to be able to place the post 322 within the interior channel 230 of the connector 200, and preferably also have enough elasticity to return to their untensioned configuration, i.e. the configuration of the first lateral member 216 and the second lateral member 218, before being urged apart.

Figure 10:
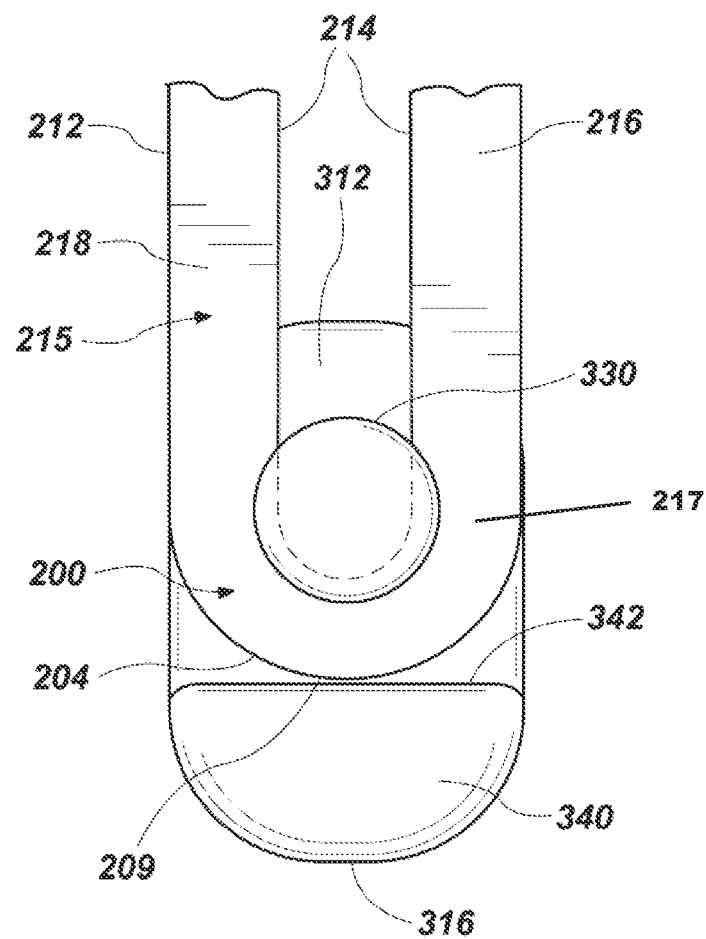
FIG. 10 is a top plan view of the connector mount of FIG. 6 attached to one end of a connector.
Figure 11:
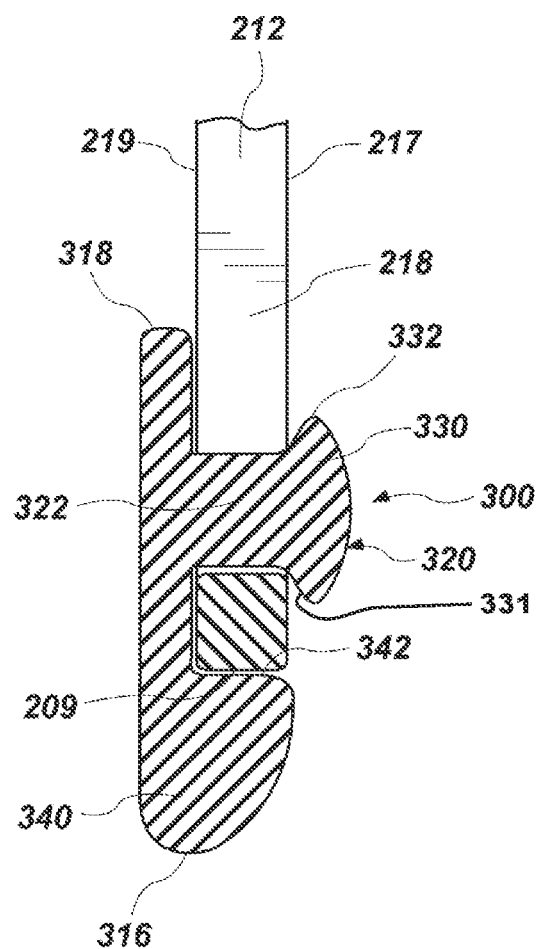
FIG. 11 is a side elevation view of the connector mount and connector of FIG. 10.

The connector mount 300 further includes a backstop 340 having an engagement surface 342 facing the post 322. The engagement surface 342 is preferably flat or substantially flat, as shown in FIG. 11 and the other illustrated embodiments, although convex configurations in which one or both of the respective ends curves away from the post 322 are also possible. The engagement surface 342 is positioned sufficiently far from the post 322 and/or the outer rim 332 of the laterally extending support 320 to allow a proximal or distal end of a lateral member 215 and/or receiving portion 210 to fit between the engagement surface 342 and the post 322, and/or between the engagement surface 342 and the outer rim 332, as shown in FIGS. 10 and 11. When the post 322 of the laterally extending support 320 is retained within a receiving portion 210 at the proximal end 202 and/or distal end 204 of the connector 200, and when the outer surface 212 of the proximal end 202 or distal end 204 faces the engagement surface 342 of the backstop 340, as shown in FIGS. 10 and 11, movement of the proximal or distal end of the connector 200 in the direction of the engagement surface 342 will be stopped by contact between the outer surface 212 of the tip 209 of the longitudinal end (202 or 204) of the connector 200 and the engagement surface 342 of the backstop 340. When the engagement surface 342 of the backstop 340 is attached to a lateral side of a tray 15 such that it is oriented approximately vertically, i.e. so that the engagement surface 342 faces anteriorly or posteriorly, as shown in FIGS. 1-3 for example, the backstop 340 will prevent the post 322 from being urged out of the receiving portion 210 and toward the medial portion 205 of the connector 200 while the present appliance 10 is being worn. In order to maintain the mandible in a relatively forward orientation, to prevent snoring and/or apnea in the embodiment of FIGS. 1-3, the backstops 340 are preferably attached in a relatively anterior position on each lateral side (right side 12 and left side 14) of the upper dental tray 120 with the engagement surfaces 342 facing posteriorly, while the backstops 340 of the lower dental tray 140 are attached in a relatively posterior position on each lateral side (right side 12 and left side 14) of the lower dental tray 140 with the engagement surfaces 342 facing anteriorly (these orientations are reversed in the embodiment of FIG. 13). This allows the upper dental tray 120 and lower dental tray 140 to be more securely connected to each other while the present appliance 10 is being worn by a subject, even when a flexible material is used as the connector 200. Such flexible material for the connector 200 allows lateral movement of a subject's jaws while wearing the present appliance 10, while the backstop 340 prevents movement of the connectors 200 in a direction that would risk dislodging the connectors from the trays 15.

Figure 5:
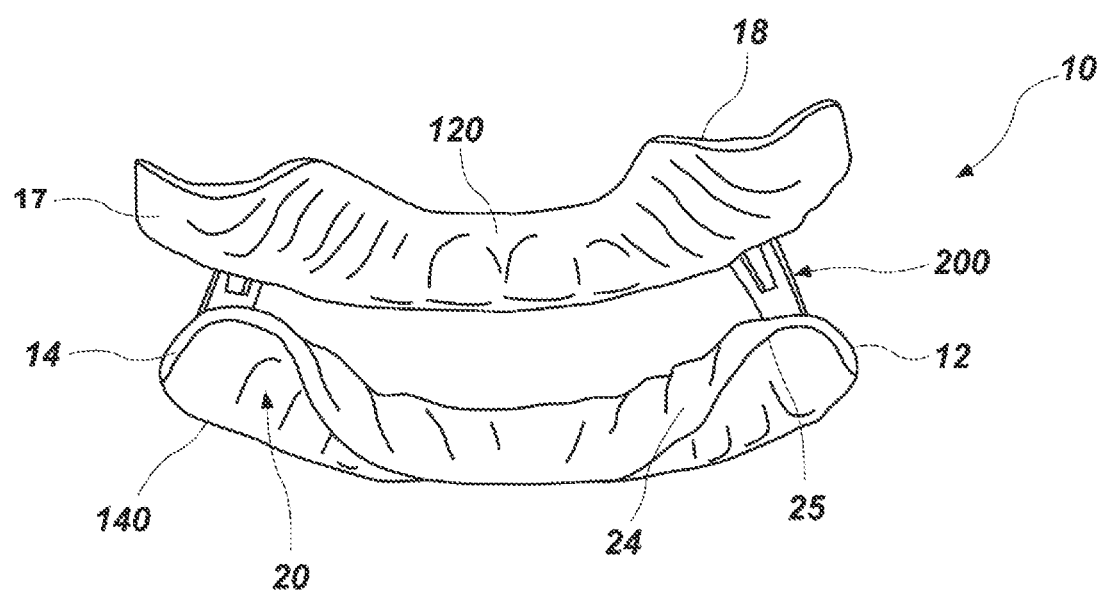
FIG. 5 is a rear elevation view of the appliance of FIG. 1.

When it is desired to remove or replace a connector 200, the post 322 can be removed from the receiving portion 210 by rotating the tip 209 of the proximal end 202 or distal end 204 of the connector 200 so that its outer surface 212 no longer faces or is adjacent to the engagement surface 342 of the backstop 340. For example, if the connector 200 shown in FIG. 5A is rotated 90° in either direction around the post 322 of the connector mount 300, then the outer surface 212 of the tip 209 no longer faces the engagement surface 342 of the backstop 340, and the connector 200 can be urged so as to move the post 322 out of the receiving portion 210. The lateral members 215 of the connector 200 can then be flexed, bent, or stretched in order to remove the connector 200 from the connector mount 300.

In a preferred embodiment, the proximal end 202 and distal end 204 of the connector 200 have the same size and form and can be used interchangeably, such that either end of the connector 200 can be attached to the upper tray 120, and likewise either end of the connector 200 can be attached to the lower tray 140. In this embodiment, the receiving portions 220 of the proximal end 202 and distal end 204 have the same or essentially the same size and shape, and the laterally extending supports 320 of the connector mounts likewise are configured to receive either longitudinal end of the connectors 200.

The dental trays 15, connectors 200, and connector mounts of the present appliances 10 can be formed from a variety of orally compatible materials, typically polymers. In one embodiment, acrylic is used to form the trays 15 and connector mounts 300 of the present appliance. Soft plastic materials which retain some flexibility can also be used to form the trays 15 and connector mounts 300. Soft plastic materials are preferred for the connectors 200, in order to allow lateral movement of a user's jaws, which is allowed by the elastic deformation of the connectors 200 when they are made from a soft plastic material.

Thermoplastic polymers are typically used to form the present appliance, but thermosets, thermoplastic elastomers, and other materials can also be used. The thermoplastic materials that are used must be capable of retaining their shape when used by a subject, and thus preferably remain solid at least at about 100° F., and preferably remain solid at somewhat higher temperatures, such as at 110° F., 120° F., or higher. When thermoplastic materials are used to form the present trays, they preferably become deformable at a temperature of 212° F. or less, so that they can be made plastic by being placed in boiling water. Preferably, the material is not deformable at less than 120° F., preferably at not less than 145° F.

In one embodiment, a soft thermoplastic material is used to form the dental trays 15 of the present appliance. In order to fit the appliance 10 to a particular subject's dentition, the soft thermoplastic material is softened in the manner of a "boil and bite" appliance, namely by placing the dental trays 15 of the appliance 10 in near-boiling water for between several seconds and one minute. The dental trays are then placed in the subject's mouth in alignment with the subject's teeth, and the subject is instructed to bite into the softened material to make an impression of the teeth in the softened material. The material is then allowed to cool in the mouth for approximately one minute, after which the appliance is preferably soaked in cold water for an additional minute.

The trays, connectors, and components thereof can also be formed in other ways known to the art, such as through vacuum-forming. Trays configured for the dentition of a particular user, such as the orthodontic trays described below, can advantageously be formed by 3D printing or by milling. In such embodiments, the shape and size of an individual's dentition can be measured, either by scanning the individual's dentition directly or by scanning a mold of the dentition. A tray with a receptacle portion 20 configured to receive the individual's dentition can then be designed by appropriate software (in the nature of CAD-CAM software) using the scanned data concerning the individual's dentition. The tray 15 can then be produced, for example, by 3D printing using a 3D printer, or by milling or machining using devices known to the art such as computer numerical control machines. Trays produced in this manner, such as by 3D-printing, are advantageously made with the connector mounts 300 integrally included in the dental trays 15. In such embodiments, the connector mount 300 need not include a base 310, as the post (laterally extending support) 322 and backstop 340 can extend directly from the exterior surface 17 of the dental trays 15, as shown in the embodiment of FIG. 12.

Orthodontic Trays

In one embodiment, the trays 15 can be formed as a series of orthodontic dental trays for use by a subject. In this embodiment, trays 15 having differently-configured receptacle portions 20 are applied to the subject over time in order to reposition individual teeth in successive steps and/or to change the configuration of a subject's mandible and/or maxilla. The successive use of a number of such dental trays 15 permits each appliance to be configured to move individual teeth in small increments, typically less than 2 mm, preferably less than 1 mm, and more preferably less than 0.5 mm (referring to the maximum linear translation of any point on a tooth as a result of using a single appliance).

The tooth-receiving receptacle portions 20 of the dental trays 15 typically have a geometry corresponding to an intermediate or end tooth arrangement intended for a subject. When such a tray 15 is first worn by the subject, certain of the teeth will be misaligned relative to an undeformed geometry of the receptacle portion 20 of a tray 15. In this embodiment, the tray 15 is formed from a material that is sufficiently resilient to accommodate or conform to the misaligned teeth, but will apply sufficient resilient force against such misaligned teeth to reposition the teeth to the intermediate or end arrangement desired for that treatment step. The appliance will preferably, but not necessarily, fit over all teeth present in the upper or lower jaw. In some cases only certain teeth will be repositioned while will provide a base or anchor region for holding the repositioning appliance in place as it applies the resilient repositioning force against the tooth or teeth to be repositioned A subject's teeth are repositioned from an initial tooth arrangement to a final tooth arrangement by placing a series of incremental position adjustment appliances in the subject's mouth. The first tray appliance of the series will have a geometry selected to reposition the teeth from the initial tooth arrangement to a first intermediate arrangement. After the first intermediate arrangement is approached or achieved, one or more additional (intermediate) appliances will be successively placed on the teeth, where such additional appliances have geometries selected to progressively reposition teeth from the first intermediate arrangement through successive intermediate arrangement(s). The treatment will be finished by placing a final appliance in the subject's mouth, where the final appliance has a geometry selected to progressively reposition teeth from the last intermediate arrangement to the final tooth arrangement.

In order to design a series of dental trays 15 that will reposition a particular subject's teeth, a digital data set representing an initial tooth arrangement and a final tooth arrangement can be determined. The initial data set representing the initial tooth arrangement, which can be presented as a visual image, is manipulated to reposition individual teeth. A final digital data set is then produced which represents the final tooth arrangement with repositioned teeth. The initial digital data set may be provided by conventional techniques, including digitizing X-ray images, images produced by computer-aided tomography (CAT scans), images produced by magnetic resonance imaging (MM), and/or by other methods known to the art for producing three-dimensional digital representations of a subject's teeth. Alternatively, the initial digital data set may be provided by producing a plaster cast of the subject's teeth (prior to treatment) by conventional techniques, for example, and the plaster cast can then be scanned using laser or other scanning equipment to produce a high resolution digital representation of the plaster cast of the subject's teeth.

Once the initial and final data sets have been determined, a series of intermediate data sets, representing intermediate tooth positions for a subject's teeth, are determined. The successive intermediate digital data sets are preferably produced by determining positional differences between selected individual teeth in the initial data set and in the final data set and interpolating the differences. Such interpolation may be performed over at least three discrete stages, embodied in three different dental trays, more often at least ten, sometimes at least twenty-five, and occasionally forty or more. The interpolation can be a linear interpolation for some or all of the positional difference, or alternatively may be nonlinear. The positional differences will correspond to tooth movements where the maximum linear movement of any point on a tooth is preferably 2 mm or less, usually 1 mm or less, and preferably 0.5 mm or less.

Once the intermediate and final data sets have been determined, the appliances can be fabricated, such as with a rapid prototyping device or digital printer. Preferably, the appliance is polymeric and is formed from a thin sheet of a suitable elastomeric polymeric, such as Tru-Tain 0.03 in. thermal forming dental material (Tru-Tain Plastics, Rochester, Minn. 55902). One structure corresponding to each of the dental tray appliances is produced.

The foregoing dental tray appliances and their use in orthodontic treatment are described in U.S. Pat. No. 5,975,893 and in other patents assigned to Align Technology, Inc., including U.S. Pat. No. 621,562, 6,217,325, 6,398,548, 6,626,666, 6,629,840, 6,699,037, 7,134,874, 7,474,307, 8,105,080, and 8,562,340.

In embodiments in which tooth or jaw repositioning is not needed or desired, such as following a successful orthodontic treatment, the upper and lower dental trays 15 can be formed in ways known to the art. For example, when the present appliance is formed from a thermoplastic polymer, the upper dental tray 120 and lower dental tray 140 can be first evaluated for their fit with a subject's mouth, after which the trays can be softened, preferably by placing the appliance in near-boiling water for between several seconds and one minute. The softened appliance is then placed in the subject's mouth in alignment with the subject's upper and lower teeth, and the subject is instructed to bite into the softened material to make an impression of the teeth in the softened material. The tray material is then allowed to cool in the mouth for approximately one minute, after which the appliance is preferably soaked in cold water for an additional minute. Creating a customized dental impression in the trays of the present appliance in other ways and using other materials can be accomplished by one of skill in the art using known methods.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure.

Recitation of value ranges herein is merely intended to serve as a shorthand method for referring individually to each separate value falling within the range. Unless otherwise indicated herein, each individual value is incorporated into the specification as if it were individually recited herein. All references cited herein, including patent applications from which the present application claims priority, are incorporated by reference in their entirety.

What is claimed is:

1. An oral appliance for treating snoring and/or sleep apnea in a subject, comprising:
  (1) an upper dental tray having an anterior portion, a posterior portion, a right side, a left side, a buccal side, a lingual side, and an exterior surface, the upper dental tray comprising:
    (a) a receptacle bounded by an inner surface of the upper dental tray for receiving the subject's maxillary dentition;
    (b) a right side laterally extending support directly attached to or integrally formed with the right side and exterior surface of the upper dental tray on the buccal side of the upper dental tray and having a proximal end and a distal end, wherein the proximal end comprises a post and the distal end comprises a flange;
    (c) a right side backstop directly attached to or integrally formed with the right side and exterior surface of the upper dental tray on the buccal side of the upper dental tray, the backstop comprising an engagement surface facing posteriorly toward the right side laterally extending support, wherein the backstop is spaced apart from the right side laterally extending support;
    (d) a left side laterally extending support directly attached to or integrally formed with the left side and exterior surface of the upper dental tray on the buccal side of the upper dental tray and having an outer surface, a proximal end and a distal end, wherein the proximal end comprises a post and the distal end comprises a flange; and
    (e) a left side backstop directly attached to or integrally formed with the left side and exterior surface of the upper dental tray on the buccal side of the upper dental tray and, the backstop comprising an engagement surface facing posteriorly toward the left side laterally extending support, wherein the backstop is spaced apart from the left side laterally extending support;
  (2) a lower dental tray having an anterior portion, a posterior portion, a right side, a left side, a buccal side, a lingual side, and an exterior surface, the lower dental tray comprising:
    (a) a receptacle bounded by the inner surface of the lower dental tray for receiving the subject's mandibular dentition;
    (b) a right side laterally extending support directly attached to or integrally formed with the right side and exterior surface of the lower dental tray on the buccal side of the lower dental tray and having an outer surface, a proximal end and a distal end, wherein the proximal end comprises a post and the distal end comprises a flange; and
    (c) a right side backstop directly attached to or integrally formed with the right side and exterior surface of the lower dental tray on the buccal side of the lower dental tray, the backstop comprising an engagement surface facing anteriorly toward the right side laterally extending support of the lower dental tray, wherein the backstop is spaced apart from the right side laterally extending support;
    (d) a left side laterally extending support directly attached to or integrally formed with the left side and exterior surface of the lower dental tray on the buccal side of the lower dental tray and having a proximal end and a distal end, wherein the proximal end comprises a post and the distal end comprises a flange;
    (e) a left side backstop directly attached to or integrally formed with the left side and exterior surface of the lower dental tray on the buccal side of the lower dental tray, the backstop comprising an engagement surface facing anteriorly toward the left side laterally extending support of the lower dental tray, wherein the backstop is spaced apart from the left side laterally extending support;
  (3) a right side connector having a proximal end, a distal end, an inner surface, an outer surface, an upper surface, a lower surface, a first lateral side, a second lateral side, an interior channel between the first lateral side and the second lateral side, a first receiving portion at the proximal end having a first opening, and a second receiving portion at the distal end having a second opening,
  wherein the right side laterally extending support of the upper dental tray fits within the first opening of the first receiving portion so that the outer surface of the laterally extending support faces the interior surface of the proximal end of the right side connector and the outer surface of the proximal end of the right side connector faces the engagement surface of the right side backstop of the upper dental tray, and
  wherein the right side laterally extending support of the lower dental tray fits within the second opening of the second receiving portion so that the outer surface of the laterally extending support faces the interior surface of the distal end of the right side connector and the outer surface of the distal end of the right side connector faces the engagement surface of the right side backstop of the lower dental tray; and
  (4) a left side connector having a proximal end, a distal end, an inner surface, an outer surface, an upper surface, a lower surface, a first lateral side, a second lateral side, an interior channel between the first lateral side and the second lateral side, a first receiving portion at the proximal end having a first opening, and a second receiving portion at the distal end having a second opening, wherein the left side laterally extending support of the upper dental tray fits within the first opening of the first receiving portion of the left side connector so that the outer surface of the laterally extending support faces the interior surface of the proximal end of the left side connector and the outer surface of the proximal end of the left side connector faces the engagement surface of the backstop of the upper dental tray, and wherein the left side laterally extending support of the lower dental tray fits within the second opening of the second receiving portion of the left side connector so that the outer surface of the laterally extending support faces the interior surface of the distal end of the left side connector and the outer surface of the distal end of the left side connector faces the engagement surface of the left side backstop of the lower dental tray, wherein the right side connector and the left side connector each comprise a first lateral member and a second lateral member, the first lateral member and the second lateral member each having an inner surface, wherein the flange of each laterally extending support is wider than the distance between the inner surface of the first lateral member and the inner surface of the second lateral member of the right side connector and the left side connector, wherein the first lateral member and the second lateral member of the right side connector are sufficiently elastically deformable to be able to fit over the flanges of the right side laterally extending supports of each of the upper dental tray and the lower dental tray and to be able place the posts of each of the right side laterally extending supports of the upper dental tray and the lower dental tray within the interior channel of the right side connector, and wherein the first lateral member and the second lateral member of the left side connector are sufficiently elastically deformable to be able to fit over the flanges of the left side laterally extending supports of each of the upper dental tray and the lower dental tray, and to place the posts of each of the right side laterally extending supports of the upper dental tray and the lower dental tray within the interior channel of the left side connector.

2. The oral appliance of claim 1, wherein each of the laterally extending supports and backstops is integrally formed with a dental tray.

3. The oral appliance of claim 1, wherein the flange of one or more of the laterally extending supports extends circumferentially around the distal end of the respective laterally extending support.

4. The oral appliance of claim 3, wherein the flange has a circular outer rim.

5. The oral appliance of claim 1, wherein the engagement surface of the backstop is substantially planar.

6. The oral appliance of claim 1, wherein the engagement surface of the backstop is radiused.

7. The oral appliance of claim 1, wherein the right side connector and the left side connector of the upper dental tray are positioned in the anterior portion of the upper dental tray adjacent to the subject's cuspid or first bicuspid, and wherein the right side connector and the left side connector of the lower dental tray are positioned in the posterior portion of the lower dental tray adjacent to the subject's first or second molar.

8. The oral appliance of claim 1, wherein the right side connector and the left side connector of the lower dental tray are positioned in the anterior portion of the upper dental tray adjacent to the subject's cuspid or first bicuspid, and wherein the right side connector and the left side connector of the upper dental tray are positioned in the posterior portion of the lower dental tray adjacent to the subject's first or second molar.

9. The oral appliance of claim 1, wherein the right side connector and/or the left side connector comprise a first lateral member and a second lateral member, and wherein the first lateral member and the second lateral member are curved.

10. The oral appliance of claim 1, wherein the receiving portions comprise at least one projection which extends inwardly from the interior surface of at least one of the connectors.

11. The oral appliance of claim 1, wherein the dental trays are formed from a soft plastic material.

12. The oral appliance of claim 1, further comprising a first orthodontic tray and a second orthodontic tray, wherein the first orthodontic tray can be received within the receptacle of the upper dental tray and the second orthodontic tray can be received within the receptacle of the lower dental tray.

13. The oral appliance of claim 1, further comprising a series of first orthodontic trays and a series of second orthodontic trays, wherein each of the orthodontic trays in the series comprises a different configuration in order to change the position of the subject's teeth and/or the shape of the subject's jaw, wherein the first orthodontic trays can be received within the receptacle of the upper dental tray and the second orthodontic trays can be received within the receptacle of the lower dental tray.

14. The oral appliance of claim 1, further comprising a series of upper dental trays and a series of lower dental trays, wherein each of the upper dental trays and lower dental trays in the series comprises a different configuration in order to change the position of the subject's teeth and/or the shape of the subject's jaw.

15. A method of treating snoring and/or sleep apnea comprising the step of providing the oral appliance of claim 1 to a subject in need thereof.

16. The method of claim 15, wherein the oral appliance comprises a series of upper dental trays and a series of lower dental trays, wherein each of the upper dental trays and the lower dental trays in the series comprises a different configuration in order to change the position of the subject's teeth and/or the shape of the subject's jaw, and wherein the series of upper dental trays and lower dental trays are provided to the subject.

17. The method of claim 15, wherein a first orthodontic tray and a second orthodontic tray are further provided, and wherein the first orthodontic tray can be received within the receptacle of the upper dental tray and the second orthodontic tray can be received within the receptacle of the lower dental tray.

18. An oral appliance for treating snoring and/or sleep apnea in a subject, comprising:
(1) an upper dental tray having an anterior portion, a posterior portion, a right side, a left side, a buccal side, a lingual side, and an exterior surface, the upper dental tray comprising:

(a) a receptacle bounded by an inner surface of the upper dental tray for receiving the subject's maxillary dentition;

(b) a right side laterally extending support directly attached to or integrally formed with the right side and exterior surface of the upper dental tray on the buccal side of the upper dental tray and having a proximal end and a distal end, wherein the proximal end comprises a post and the distal end comprises a flange;

(c) a right side backstop directly attached to or integrally formed with the right side and exterior surface of the upper dental tray on the buccal side of the upper dental tray, the backstop comprising an engagement surface facing anteriorly toward the right side laterally extending support, wherein the backstop is spaced apart from the right side laterally extending support;

(d) a left side laterally extending support directly attached to or integrally formed with the left side and exterior surface of the upper dental tray on the buccal side of the upper dental tray and having an outer surface, a proximal end and a distal end, wherein the proximal end comprises a post and the distal end comprises a flange; and (e) a left side backstop directly attached to or integrally formed with the left side and exterior surface of the upper dental tray on the buccal side of the upper dental tray and, the backstop comprising an engagement surface facing anteriorly toward the left side laterally extending support, wherein the backstop is spaced apart from the left side laterally extending support;

(2) a lower dental tray having an anterior portion, a posterior portion, a right side, a left side, a buccal side, a lingual side, and an exterior surface, the lower dental tray comprising:

(a) a receptacle bounded by the inner surface of the lower dental tray for receiving the subject's mandibular dentition;

(b) a right side laterally extending support directly attached to or integrally formed with the right side and exterior surface of the lower dental tray on the buccal side of the lower dental tray and having an outer surface, a proximal end and a distal end, wherein the proximal end comprises a post and the distal end comprises a flange; and (c) a right side backstop directly attached to or integrally formed with the right side and exterior surface of the lower dental tray on the buccal side of the lower dental tray, the backstop comprising an engagement surface facing posteriorly toward the right side laterally extending support of the lower dental tray, wherein the backstop is spaced apart from the right side laterally extending support;

(d) a left side laterally extending support directly attached to or integrally formed with the left side and exterior surface of the lower dental tray on the buccal side of the lower dental tray and having a proximal end and a distal end, wherein the proximal end comprises a post and the distal end comprises a flange;

(e) a left side backstop directly attached to or integrally formed with the left side and exterior surface of the lower dental tray on the buccal side of the lower dental tray, the backstop comprising an engagement surface facing posteriorly toward the left side laterally extending support of the lower dental tray, wherein the backstop is spaced apart from the left side laterally extending support;

(3) a right side connector having a proximal end, a distal end, an inner surface, an outer surface, an upper surface, a lower surface, a first lateral side, a second lateral side, an interior channel between the first lateral side and the second lateral side, a first receiving portion at the proximal end having a first opening, and a second receiving portion at the distal end having a second opening, wherein the right side laterally extending support of the upper dental tray fits within the first opening of the first receiving portion so that the outer surface of the laterally extending support faces the interior surface of the proximal end of the right side connector and the outer surface of the proximal end of the right side connector faces the engagement surface of the right side backstop of the upper dental tray, and wherein the right side laterally extending support of the lower dental tray fits within the second opening of the second receiving portion so that the outer surface of the laterally extending support faces the interior surface of the distal end of the right side connector and the outer surface of the distal end of the right side connector faces the engagement surface of the right side backstop of the lower dental tray; and (4) a left side connector having a proximal end, a distal end, an inner surface, an outer surface, an upper surface, a lower surface, a first lateral side, a second lateral side, an interior channel between the first lateral side and the second lateral side, a first receiving portion at the proximal end having a first opening, and a second receiving portion at the distal end having a second opening, wherein the left side laterally extending support of the upper dental tray fits within the first opening of the first receiving portion of the left side connector so that the outer surface of the laterally extending support faces the interior surface of the proximal end of the left side connector and the outer surface of the proximal end of the left side connector faces the engagement surface of the backstop of the upper dental tray, and wherein the left side laterally extending support of the lower dental tray fits within the second opening of the second receiving portion of the left side connector so that the outer surface of the laterally extending support faces the interior surface of the distal end of the left side connector and the outer surface of the distal end of the left side connector faces the engagement surface of the left side backstop of the lower dental tray, wherein the right side connector and the left side connector each comprise a first lateral member and a second lateral member, the first lateral member and the second lateral member each having an inner surface, wherein the flange of each laterally extending support is wider than the distance between the inner surface of the first lateral member and the inner surface of the second lateral member of the right side connector and the left side connector, wherein the first lateral member and the second lateral member of the right side connector are sufficiently elastically deformable to be able to fit over the flanges of the right side laterally extending supports of each of the upper dental tray and the lower dental tray and to be able place the posts of each of the right side laterally extending supports of the upper dental tray and the lower dental tray within the interior channel of the right side connector, and wherein the first lateral member and the second lateral member of the left side connector are sufficiently elastically deformable to be able to fit over the flanges of the left side laterally extending supports of each of the upper dental tray and the lower dental tray, and to place the posts of each of the right side laterally extending supports of the upper dental tray and the lower dental tray within the interior channel of the left side connector.

19. The oral appliance of claim 18, further comprising a first orthodontic tray and a second orthodontic tray, wherein the first orthodontic tray can be received within the receptacle of the upper dental tray and the second orthodontic tray can be received within the receptacle of the lower dental tray.

20. The oral appliance of claim 18, further comprising a series of first orthodontic trays and a series of second orthodontic trays, wherein each of the orthodontic trays in the series comprises a different configuration in order to change the position of the subject's teeth and/or the shape of the subject's jaw, wherein the first orthodontic trays can be received within the receptacle of the upper dental tray and the second orthodontic trays can be received within the receptacle of the lower dental tray.

21. The oral appliance of claim 18, further comprising a series of upper dental trays and a series of lower dental trays, wherein each of the upper dental trays and lower dental trays in the series comprises a different configuration in order to change the position of the subject's teeth and/or the shape of the subject's jaw.

22. A method of treating snoring and/or sleep apnea comprising the step of providing the oral appliance of claim 18 to a subject in need thereof.

23. The method of claim 22, wherein the oral appliance comprises a series of upper dental trays and a series of lower dental trays, wherein each of the upper dental trays and the lower dental trays in the series comprises a different configuration in order to change the position of the subject's teeth and/or the shape of the subject's jaw, and wherein the series of upper dental trays and lower dental trays are provided to the subject.

24. The method of claim 22, wherein a first orthodontic tray and a second orthodontic tray are further provided, and wherein the first orthodontic tray can be received within the receptacle of the upper dental tray and the second orthodontic tray can be received within the receptacle of the lower dental tray.

* * * * *